United States Patent
Blatt et al.

(10) Patent No.: US 10,682,534 B2
(45) Date of Patent: Jun. 16, 2020

(54) COSMETIC PREPARATIONS CONTAINING CREATINE AND/OR CREATININE AND ORGANIC THICKENERS

(75) Inventors: Thomas Blatt, Wedel (DE); Thomas Raschke, Pinneberg (DE); Christopher Mummert, Bienenbüttel (DE); Volker Kallmayer, Hamburg (DE)

(73) Assignee: Beiersdorf, AG, Hamburg (DE)

( * ) Notice: Subject to any disclaimer, the term of this patent is extended or adjusted under 35 U.S.C. 154(b) by 2317 days.

(21) Appl. No.: 10/995,208

(22) Filed: Nov. 24, 2004

(65) Prior Publication Data

US 2005/0142154 A1    Jun. 30, 2005

(30) Foreign Application Priority Data

Nov. 26, 2003    (DE) .................. 103 55 716

(51) Int. Cl.
  *A61Q 19/00*    (2006.01)
  *A61K 31/198*    (2006.01)
  *A61K 8/44*    (2006.01)
  *A61K 8/81*    (2006.01)
  *A61Q 17/00*    (2006.01)
  *A61Q 19/08*    (2006.01)
  *A61K 8/73*    (2006.01)

(52) U.S. Cl.
  CPC .......... *A61Q 19/00* (2013.01); *A61K 8/44* (2013.01); *A61K 8/73* (2013.01); *A61K 8/8152* (2013.01); *A61K 31/198* (2013.01); *A61Q 17/00* (2013.01); *A61Q 19/08* (2013.01)

(58) Field of Classification Search
  CPC ...................................................... A61K 8/44
  See application file for complete search history.

(56) References Cited

U.S. PATENT DOCUMENTS

| | | | |
|---|---|---|---|
| 4,590,067 A | 5/1986 | Meisner | |
| 4,647,453 A | 3/1987 | Meisner | |
| 5,091,171 A | 3/1992 | Yu et al. | |
| 5,834,513 A | 11/1998 | Ptchelintsev et al. | |
| 5,939,078 A | 8/1999 | Fujimura et al. | |
| 6,166,249 A | 12/2000 | Pischel et al. | |
| 6,172,111 B1 | 1/2001 | Pischel et al. | |
| 6,242,491 B1 | 6/2001 | Kaddurah-Daouk | |
| 6,355,752 B1 * | 3/2002 | Brungs et al. ............. | 526/287 |
| 6,413,552 B1 | 7/2002 | Stoll | |
| 6,432,424 B1 | 8/2002 | Shapiro et al. | |
| 6,524,611 B2 * | 2/2003 | Howard .................. | A23L 2/39 424/439 |
| 7,150,880 B2 | 12/2006 | Howard et al. | |
| 2002/0048603 A1 * | 4/2002 | Burmeister et al. ......... | 424/486 |
| 2002/0049253 A1 | 4/2002 | Kaddurah-Daouk | |
| 2002/0182234 A1 * | 12/2002 | Riedel et al. .............. | 424/401 |
| 2003/0147928 A1 | 8/2003 | Zelle et al. | |
| 2004/0018162 A1 | 1/2004 | Bimczok et al. | |
| 2004/0029969 A1 | 2/2004 | Blatt et al. | |
| 2004/0052749 A1 | 3/2004 | Golz-Berner et al. | |
| 2004/0197279 A1 * | 10/2004 | Bleckmann et al. .......... | 424/59 |
| 2004/0241197 A1 | 12/2004 | Biergiesser et al. | |
| 2004/0258717 A1 | 12/2004 | Sauermann et al. | |
| 2006/0018869 A1 | 1/2006 | Stab et al. | |

FOREIGN PATENT DOCUMENTS

| | | | |
|---|---|---|---|
| DE | 10032964 | 1/2002 | |
| DE | 10119608 | 10/2002 | |
| DE | 10136076 | 2/2003 | |
| DE | 10157199 | 6/2003 | |
| DE | 10244281 | 4/2004 | |
| EP | 178602 | 4/1986 | |
| EP | 565010 | 10/1993 | |
| FR | 2725896 | 4/1996 | |
| FR | 2734721 | 12/1996 | |
| JP | 9-202709 | 8/1997 | |
| JP | 9-202710 | 8/1997 | |
| JP | 9-263511 | 10/1997 | |
| JP | 2000-247866 | 9/2000 | |
| JP | 2000247866 A * | 9/2000 | ............... A61K 7/48 |
| WO | 98/28263 | 7/1998 | |
| WO | 98/53704 A1 | 12/1998 | |
| WO | 00/15187 | 3/2000 | |
| WO | 00/33787 | 6/2000 | |
| WO | 07/00203 | 1/2001 | |
| WO | 02/02075 | 1/2002 | |
| WO | 02060394 | 8/2002 | |
| WO | 02/076408 | 10/2002 | |
| WO | 03/005988 | 1/2003 | |
| WO | 03/011241 A1 | 2/2003 | |
| WO | 2004/064801 | 8/2004 | |

OTHER PUBLICATIONS

English language Abstract of DE 10244281.
A. Deflandre and G. Lang, International Journal of Cosmetic Science, 10, 53-62 (1988).
A. Voelckel et al., Zentralblatt Haut- und Geschlechtskrankheiten, 156, 1-15 (1989).
Y. Miyachi "Skin Diseases Associated with Oxidative Injury" in "Oxidative Stress in Dermatology", edited by J. Fuchs and L. Packer, Marcel Dekker, Inc., New York, Basel, Hong Kong, 1993, pp. 323-331.
English language Abstract of DE 10119608.
English language Abstract of JP 2000-247866.
H.P. Fiedler "Lexikon der Hilfsstoffe für Pharmazie, Kosmetik und angrenzende Gebiete", 3. überarbeitete und ergänzte Auflage, Editio Cantor Aulendorf, 1989, pp. 293-294.

(Continued)

*Primary Examiner* — Kyle A Purdy

(74) *Attorney, Agent, or Firm* — Abel Schillinger, LLP

(57) ABSTRACT

A combination comprising creatine and/or creatinine and/or a derivative thereof and one or more hydrocolloids. This Abstract is not intended to define the invention disclosed in the specification, nor intended to limit the scope of the invention in any way.

37 Claims, No Drawings

(56) References Cited

OTHER PUBLICATIONS

English Language Abstract of JP 9-202709.
English Language Abstract of JP 9-202710.
English Language Abstract of JP 9-263511.
English Language Abstract of FR 2725896.
English Language Abstract of FR 2734721.
"The Equilibrium Between Creatine and Creatinine, in Aqueous Solution. The Effect of Hydrogen Ion"; Graham Edgar, H. E. Shiver; J. Am. Chem. Soc., 1925, 47(4), pp. 1179-1188; Apr. 1925.

* cited by examiner

COSMETIC PREPARATIONS CONTAINING CREATINE AND/OR CREATININE AND ORGANIC THICKENERS

CROSS-REFERENCE TO RELATED APPLICATIONS

The present application claims priority under 35 U.S.C. § 119 of German Patent Application No. 103 55 716.4, filed Nov. 26, 2003, the disclosure of which is expressly incorporated by reference herein in its entirety.

BACKGROUND OF THE INVENTION

1. Field of the Invention

The present invention relates to the use of creatine and/or creatine derivatives and/or creatinine and/or creatinine derivatives in cosmetic or dermatological preparations for the treatment and prophylaxis of the symptoms of UV and/or ozone-induced skin damage and of inflammatory and degenerative skin conditions.

2. Discussion of Background Information

Cosmetic skin care is primarily understood to mean strengthening or restoring the natural function of the skin as a barrier against environmental influences (for example, dirt, chemicals, microorganisms) and against the loss of endogenous substances (for example, water, natural fats, electrolytes).

Impairment of this function may lead to increased resorption of toxic or allergenic substances or to attack by microorganisms, resulting in toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin aging.

Chronological skin aging is caused, for example, by endogenous, genetically determined factors. The following structural damage and functional disorders can arise, also under the term "senile xerosis", for example, in the epidermis and the dermis as a result of aging:

a) Dryness, roughness and formation of dryness wrinkles,
b) Itching and altered pore structure of the skin
c) Reduced regreasing by sebaceous glands (e.g. after washing).

Exogenous factors, such as UV light and chemical noxae, can have a cumulative effect and, for example, accelerate or supplement the endogenous aging processes. In the epidermis and dermis, for example, the following structural damage and functional disorders arise in the skin in particular as a result of exogenous factors; these are more far-reaching than the degree and quality of the damage in the case of chronological aging:

d) Visible vascular dilation (teleangiectases, cuperosis);
e) Flaccidity and formation of wrinkles;
f) Local hyperpigmentation, hypopigmentation and abnormal pigmentation (e.g., senile keratoses) and
g) Increased susceptibility to mechanical stress (e.g., cracking).

The present invention relates in particular to products for the care of skin that has aged naturally and to the treatment of secondary damage from light-aging, in particular the phenomena listed under a) through g).

Products for the care of aged skin are known per se. They comprise, for example, retinoids (vitamin A acid and/or derivatives thereof) or vitamin A and/or derivatives thereof. Their effect on structural damage is, however, limited. Furthermore, in product development, there are considerable difficulties in stabilizing the active ingredients to an adequate extent against oxidative decay. The use of products containing vitamin A acid, moreover, often causes severe erythematous skin irritations. Retinoids can therefore only be used in low concentrations.

In particular, the present invention relates to cosmetic preparations with an effective protection against harmful oxidation processes in the skin, but also to the protection of cosmetic preparations themselves or to the protection of the constituents of cosmetic preparations against harmful oxidation processes.

The harmful effect of the ultraviolet part of solar radiation on the skin is generally known. Whereas rays with a wavelength of less than about 290 nm (the so-called UVC range) are absorbed by the ozone layer in the earth's atmosphere, rays in the range between about 290 nm and about 320 nm, the so-called UVB range, cause erythema, simple sunburn or even burns of greater or lesser severity.

The narrower range around 308 nm is indicated to be the maximum of the erythematous effect of sunlight.

Numerous compounds are known for protecting against UVB radiation; these are derivatives of 3-benzylidene camphor, of 4-aminobenzoic acid, of cinnamic acid, of salicylic acid, of benzophenone and also of 2-phenylbenzimidazole.

It is also important to have available filter substances for the range between about 320 nm and about 400 nm, the so-called UVA region, since its rays can cause reactions in cases of photosensitive skin. It has been found that UVA radiation leads to damage of the elastic and collagen fibers of connective tissue, which results in premature aging of the skin, and is to be regarded as a cause of numerous phototoxic and photoallergic reactions. The harmful effect of UVB radiation can be intensified by UVA radiation.

To protect against rays of the UVA region, therefore, certain derivatives of dibenzoylmethane are used, the photostability of which is inadequate (Int. J. Cosm. Science 10, 53 (1988), the entire disclosure whereof is expressly incorporated by reference herein).

The UV radiation can, however, also lead to photochemical reactions, in which case the photochemical reaction products again interfere with the skin's metabolism.

Corresponding photochemical reaction products are primarily free-radical compounds, for example hydroxyl radicals. Undefined free-radical photoproducts which form in the skin itself can also result in uncontrolled secondary reactions due to their high reactivity. Furthermore, singlet oxygen, a non-free-radical excited state of the oxygen molecule, can also arise during UV irradiation, as can short-lived epoxides and many others. Singlet oxygen, for example, differs from triplet oxygen (free-radical ground state), which is normally present, by its increased reactivity. However, excited, reactive (free-radical) triplet states of the oxygen molecule also exist.

UV radiation is also a type of ionizing radiation. There is therefore the risk that ionic species will also form during UV exposure, which then for their part are able to interfere oxidatively with the biochemical processes.

In order to prevent these reactions, additional antioxidants and/or free-radical scavengers can be incorporated into the cosmetic or dermatological formulations.

It would be advantageous to have available cosmetically, dermatologically and pharmaceutically active substances and preparations as well as sunscreen formulations that are used for the prophylaxis and treatment of photosensitive skin, in particular photodermatoses, preferably the polymorphous light dermatosis.

Further terms for polymorphous light dermatosis are PLD, PLE, Mallorca acne and numerous other terms as given in the literature (e.g., A. Voelckel et al., *Zentralblatt Haut-und Geschlechtskrankheiten* (1989), 156, p. 2, the entire disclosure whereof is expressly incorporated by reference herein).

Antioxidants are mainly used as substances which protect against the deterioration of the preparations in which they are present. Nevertheless, it is known that in human and animal skin undesired oxidation processes can occur as well. Such processes play an important role in skin aging.

The article "Skin Diseases Associated with Oxidative Injury" in "Oxidative Stress in Dermatology", p. 323 ff. (Marcel Decker Inc., New York, Basel, Hong Kong, Editor: Jürgen Fuchs, Frankfurt, and Lester Packer, Berkeley/Calif.), the entire disclosure whereof is expressly incorporated by reference herein, discusses oxidative skin damage and its more direct causes.

Also for the reason of preventing such reactions, antioxidants and/or free-radical scavengers can be additionally incorporated into cosmetic or dermatological formulations.

The advantageous prophylactic and therapeutic effect of creatine in cosmetic and medical skin care is known per se. Creatine (from the Greek: το κρεας ="the meat") is characterized by the following structure:

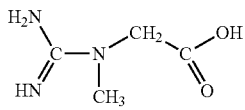

Creatine is found in the myoserum of vertebrates in amounts of 0.05-0.4%, in small amounts also in the brain and blood. As a monohydrate, it is a colorless, crystalline powder. In aqueous solution, creatinine is formed. In the organism, it is formed by the transamidination of L-arginine on glycine to afford guanidinoacetic acid, and subsequent methylation thereof by means of S-adenosyl methionine (by guanidinoacetate methyltransferase). Creatine is regarded as an appetite-promoting constituent of beef and meat extract. The addition of creatine to the diet enhances physical performance.

The prior art is extensive on the cosmetic and dermatological uses of creatine. Thus, DE 100 32 964, the entire disclosure whereof is expressly incorporated by reference herein, describes the use of creatine and/or creatine derivatives in cosmetic or dermatological preparations for the treatment and prophylaxis of the symptoms of UV-induced and/or ozone-induced skin damage and of inflammatory and degenerative skin conditions.

JP 2000/247,866, the entire disclosure whereof is expressly incorporated by reference herein, describes skin cosmetics with a content of creatine and/or creatinine which can be used as a cream or as a milky lotion, where excellent skin care properties are attributed to the relevant preparations.

Furthermore, WO 00/33787, the entire disclosure whereof is expressly incorporated by reference herein, describes the use of creatinine as an effective constituent of deodorants.

Moreover, EP-A-565 010, the entire disclosure whereof is expressly incorporated by reference herein, describes hair growth and hair dye preparations with a content of creatinine phosphate.

Finally, U.S. Pat. No. 4,590,067 and EP-A-178 602, the entire disclosures whereof are expressly incorporated by reference herein, describe the use of creatine or creatinine to produce preparations with anti-inflammatory effect.

However, there is the disadvantage that in aqueous products creatine and creatinine crystallize easily, whereby crystals with non-cosmetic impression form and the effectiveness of the product is reduced.

It is desirable to find ways of avoiding the disadvantages of the prior art. In particular, the effect of remedying the damage associated with endogenous, chronological and exogenous skin aging and the prophylaxis should be durable, sustained and without the risk of side effects.

It would further be advantageous to find a form of administering creatine that is characterized by a reduced tendency to form creatine crystals.

SUMMARY OF THE INVENTION

The present invention provides a cosmetic or dermatological preparation which comprises an effective amount of
(a) creatine and/or creatinine and/or a creatine derivative and/or a creatinine derivative, and
(b) one or more hydrocolloids.

In one aspect, the preparation may comprise from about 0.001% to about 10% by weight, e.g., from about 0.01% to about 1% by weight of creatine and/or a creatine derivative and/or the preparation may comprise from about 0.001% to about 10% by weight, e.g., from about 0.01% to about 1% by weight of creatinine and/or a creatinine derivative, based on the total weight of the preparation.

In another aspect, the preparation may further comprise from about 0.001% to about 30% by weight, e.g., from about 0.01% to about 15% by weight, or from about 1% to about 7% by weight of glycerin, based on the total weight of the preparation.

In yet another aspect, the weight ratio of creatinine to creatine may be from about 10:1 to about 1:10, e.g., from about 4:1 to about 3:7, or from about 2:1 to about 1:2.

In a still further aspect, the preparation may comprise less than about 1.5% by weight of the one or more hydrocolloids, e.g., not more than about 1.0% by weight of the one or more hydrocolloids and/or at least about 0.1% by weight of the one or more hydrocolloids, based on the total weight of the preparation.

In another aspect of the preparation, the one or more hydrocolloids may comprise one or more of
a) organic, fully synthetic compounds of polyacrylic acids,
b) copolymers and crosspolymers of polyacrylic acid derivatives
c) ammonium dimethyltauramide/vinylformamide copolymer
d) copolymers/crosspolymers comprising acryloyldimethyltaurate
e) hydrophilic gums and hydrophilic derivatives thereof
f) cellulose, cellulose derivatives and microcrystalline cellulose.

In another aspect, the one or more hydrocolloids may comprise one or more polyacrylates selected from carbopols of types 980, 981, 1382, 2984 and 5984 and carbomer ULTREZ.

In another aspect, the one or more hydrocolloids may comprise one or more of a polymethacrylate, an acrylate copolymer, an alkylacrylate copolymer, a polyacrylamide, an alkylacrylate crosspolymer, an acrylonitrogen copolymer and a polyacryloyldimethyltauramide.

In another aspect, the one or more hydrocolloids may comprise one or more of agar agar, alginic acid, carrageen, gelatin, gum arabic, pectin and tragacanth and/or one or more of guar gum, locust bean flour, xanthan gum, polyvinyl alcohol, polyvinylpyrrolidone, propyleneglycol alginate and starch.

In yet another aspect, the one or more hydrocolloids may comprise an alkyl-modified cellulose derivative and/or an alkylhydroxycellulose, for example, at least one of methylcellulose, hydroxypropylmethylcellulose and hydroxyethylcellulose.

In a still further aspect, the preparation may comprise at least one aqueous phase. For example, the preparation may comprise an aqueous phase which comprises creatine, creatinine, a creatine derivative and/or a creatinine derivative and has a pH value of from about 6.0 to about 8.0, e.g., a pH value of from about 6.2 to about 7.8, or a pH value of from about 6.5 to about 7.5.

The present invention also provides a cosmetic or dermatological preparation which comprises creatine, creatinine, a creatine derivative and/or a creatinine derivative and not more than about 1.5% by weight of one or more hydrocolloids. The hydrocolloids are selected from:
 a) organic, fully synthetic compounds of polyacrylic acids,
 b) copolymers and crosspolymers of polyacrylic acid derivatives
 c) ammonium dimethyltauramide/vinylformamide copolymer
 d) copolymers/crosspolymers comprising acryloyldimethyltaurate
 e) hydrophilic gums and hydrophilic derivatives thereof
 f) cellulose, cellulose derivatives and microcrystalline cellulose.

In one aspect of the preparation, the weight ratio of creatinine to creatine may be from about 10:1 to about 1:10, e.g., from about 4:1 to about 3:7, or from about 2:1 to about 1:2.

In another aspect, the preparation may comprise from about 0.01% to about 1% by weight of creatine and/or a creatine derivative and/or from about 0.01% to about 1% by weight of creatinine and/or a creatinine derivative.

In another aspect, the preparation may further comprise from about 0.001% to about 30% by weight, e.g., from about 0.01% to about 15% by weight, or from about 1% to about 7% by weight of glycerin.

In yet another aspect, the preparation may comprise at least about 0.1% and/or not more than about 1.0% by weight of the one or more hydrocolloids.

In a still further aspect, the one or more hydrocolloids may comprise carbomer ULTREZ and/or at least one of agar agar, alginic acid, carrageen, gelatin, gum arabic, pectin and tragacanth and/or at least one of guar gum, locust bean flour, xanthan gum, polyvinyl alcohol, polyvinylpyrrolidone, propyleneglycol alginate and starch and/or at least one of methylcellulose, hydroxypropylmethylcellulose and hydroxyethylcellulose.

In another aspect, the preparation may comprise an aqueous phase which comprises creatine, creatinine, a creatine derivative and/or a creatinine derivative and may have a pH value of from about 6.5 to about 7.5.

The present invention also provides an emulsion, e.g., an O/W emulsion, and a hydrogel which comprise the preparation of the present invention, including the various aspects thereof, as set forth above.

The present invention also provides a method for the prophylaxis or treatment of UV or ozone-induced skin damage and a method for the prophylaxis or treatment of inflammatory and degenerative skin. These methods comprise the application to at least a part of the skin of the preparation of the present invention, including the various aspects thereof.

A cosmetic or dermatological preparation according to the invention preferably comprises from about 0.001%, e.g., from about 0.01%, to about 10%, e.g., to about 1% by weight of creatine and/or creatine derivatives, based on the total weight of the preparation.

If derivatives of creatine are used, the preferred derivative is creatine phosphate, which has the following structure:

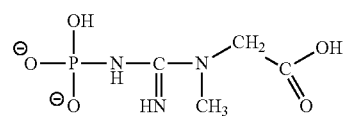

Creatine phosphate is present in fresh muscle where it plays an important role as an energy-storing phosphate (phosphagen). In the working muscle, adenosine 5'-triphosphate (ATP) and creatine are formed from creatine phosphate and adenosine 5'-diphosphate under the influence of the enzyme creatine kinase. In the resting muscle the reverse reaction takes place.

Additionally, creatine sulfate, creatine acetate, creatine ascorbate and the derivatives esterified on the carboxyl group with mono- or polyfunctional alcohols are further non-limiting examples of advantageous creatine derivatives for use in the present invention.

Creatinine (likewise from the Greek: το κρεας = "the meat") is characterized by the following structure:

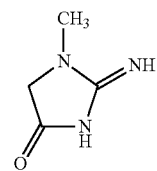

It is formed in the organism through nonenzymatic conversion of creatine phosphate according to the equation:

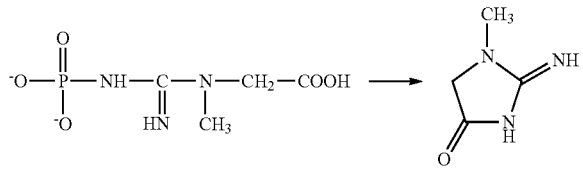

and is secreted through the kidneys. The amount of the creatinine secretion is proportional to the muscle mass and is virtually constant for each individual. Creatinine is contained in meat extract and meat broth cubes.

A cosmetic or dermatological preparation according to the invention preferably comprises from about 0.001%, or from about 0.01% to about 10%, e.g., to about 1% by weight of creatinine and/or creatinine derivatives, based on the total weight of the preparation.

According to the present invention, creatine may advantageously be used without the presence of creatinine, and creatinine may advantageously be used without the presence of creatine. However, it is particularly advantageous to use both substances simultaneously in the active substance combinations and preparations according to the present invention, in particular if the weight ratio of creatinine to creatine is selected from about 10:1 to about 1:10, preferably from about 4:1 to about 3:7, more preferably from about 2:1 to about 1:2.

"Hydrocolloid" is the technical abbreviation for the more correct term "hydrophilic colloid". Hydrocolloids are macromolecules which have a largely linear structure and exhibit intermolecular forces of interaction, which permit secondary and primary valence bonds between the individual molecules and thus the formation of a reticular structure. Some are water-soluble natural or synthetic polymers which, in aqueous systems, form gels or viscous solutions. They increase the viscosity of the water by either binding water molecules (hydration) or else by absorbing and encapsulating the water into their interwoven macromolecules, at the same time restricting the mobility of the water. Such water-soluble polymers represent a large group of chemically very different natural and synthetic polymers, the common feature of which is their solubility in water or aqueous media. The prerequisite for this is that these polymers have a sufficient number of hydrophilic groups for water solubility and are not too highly cross-linked. The hydrophilic groups can be of a nonionic, anionic or cationic nature, e.g., as follows:

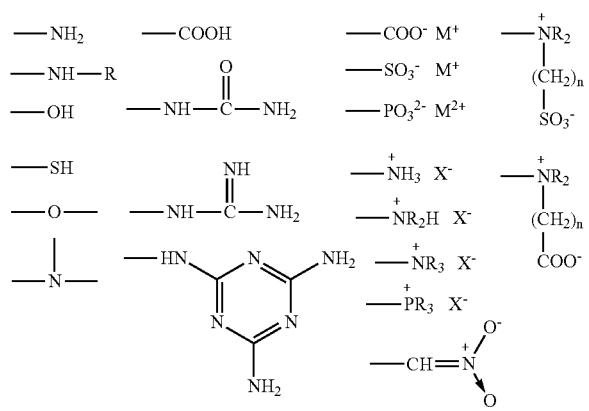

The group of cosmetically and dermatologically relevant hydrocolloids can be divided as follows:
- organic, natural compounds, such as, for example, agar agar, carrageen, tragacanth, gum arabic, alginates, pectins, polyoses, guar flour, carob bean flour, starch, dextrins, gelatins, casein,
- organic, modified natural substances, such as, for example, carboxymethylcellulose and other cellulose ethers, hydroxyethyl and hydroxypropylcellulose and the like,
- organic, completely synthetic compounds, such as, for example, polyacrylic and polymethacrylic compounds, vinyl polymers, polycarboxylic acids, polyethers, polyimines, polyamides, polyvinylpyrrolidone,
- inorganic compounds, such as, for example, polysilicic acids, clay minerals such as montmorillonites, zeolites, hectorites, silicas.

Examples of hydrocolloids which are preferred according to the invention are methylcelluloses, which is the name for the methyl ethers of cellulose. They are characterized by the following structural formula

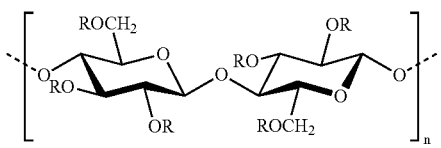

in which R can be a hydrogen or a methyl group.

Particularly advantageous for the purposes of the present invention are the cellulose mixed ethers, which are generally likewise referred to as methylcelluloses, which contain, in addition to a predominant content of methyl groups, also 2-hydroxyethyl, 2-hydroxypropyl or 2-hydroxybutyl groups. Particular preference is given to (hydroxypropyl) methylcelluloses, for example those available under the trade name Methocel E4M from Dow Chemical Comp.

Also advantageous according to the invention is sodium carboxymethylcellulose, the sodium salt of the glycolic ether of cellulose, for which R in structural formula I can be a hydrogen and/or $CH_2$—COONa. Particular preference is given to the sodium carboxymethylcellulose available under the trade name Natrosol Plus 330 CS from Aqualon and also referred to as cellulose gum.

Also preferred for the purposes of the present invention is xanthan (CAS No. 11138-66-2), also called xanthan gum, which is an anionic heteropolysaccharide, which is generally formed by fermentation from maize sugar and is isolated as potassium salt. It is produced from *Xanthomonas campestris* and some other species under aerobic conditions with a molecular weight of from $2\times10^6$ to $24\times10^6$. Xanthan is formed from a chain having β-1,4-bonded glucose (cellulose) with side chains. The structure of the subgroups comprises glucose, mannose, glucuronic acid, acetate and pyruvate. Xanthan is the designation of the first anionic heteropolysaccharide of microbial origin. It is produced by *Xanthomonas campestris* and a few other species under aerobic conditions with a molecular weight of about 2-15× $10^6$. The number of pyruvate units determines the viscosity of the xanthan. Xanthan is produced in two-day batch cultures with a yield of 70-90%, based on the carbohydrate employed. Yields of 25-30 g/l are achieved. Processing takes place after killing the culture by precipitation with, for example, 2-propanol. Xanthan is subsequently dried and powdered.

Another example of an advantageous gel-forming agent for the purposes of the present invention is carrageen, a gel-forming agent with a structure similar to that of agar. Carageen constitutes an extract from North Atlantic red algae belonging to the genus florideans (*Chondrus crispus* and *Gigartina stellata*).

The designation carrageen is frequently used for the dried algae product, and the designation carrageenan is used for the extract thereof. The carrageen precipitated from the hot water extract of the algae is a colorless to sand-colored powder with a molecular weight ranging from 100,000-800,000 and a sulfate content of approximately 25%. Carrageen is very readily soluble in warm water; upon cooling, a thixotropic gel forms even at a water content of 95-98%. The firmness of the gel results from the double helix structure of the carrageen. Three principal constituents are distinguished in carrageenan: the gel-forming κ-fraction consists of D-galactose-4-sulfate and 3,6-anhydro-α-D-galactose which are bonded together by glycosidic bonds alternating in the 1,3- and 1,4-positions (agar, by contrast, contains 3,6-anhydro-α-L-galactose). The non-gelling λ-fraction is composed of 1,3-glycosidically bonded D-galactose-2-sulfate and 1,4- bonded D-galactose-2,6-disulfate radicals, and is readily soluble in cold water. The 1-carrageenan, constituted by 1,3-bonded D-galactose-4-sulfate and 1,4-bonded 3,6 anhydro-α-D-galactose-2-sulfate, is both water-soluble and gel-forming. Further carrageen types are likewise identified by Greek letters: α, β, γ, μ, ν, ξ, π, ω, χ. The type of cations present ($K^+$, $NH_4^+$, $Na^+$, $Mg^{2+}$, $Ca^{2+}$) also affects the solubility of the carrageens.

The use of chitosan in cosmetic preparations is known per se. Chitosan is a partially deacylated chitin. This biopolymer has, i.a., film-forming properties and is characterized by a silky feel on the skin. However, a disadvantage is its great stickiness on the skin which occurs in particular—temporarily—during application. Corresponding preparations may not be marketable in individual cases, since they are not accepted by the consumer or are given a negative assessment. As is known, chitosan is used, for example, in hair care. It is suitable, more so than the chitin on which it is based, as a thickener or stabilizer and improves the adhesion and water resistance of polymeric films. Exemplary for the large number of literature references which discuss chitosan is H. P. Fiedler, "Lexikon der Hilfsstoffe für Pharmazie, Kosmetik und angrenzende Gebiete", 3rd Edition 1989, Editio Cantor, Aulendorf, p. 293, keyword "Chitosan", the entire disclosure whereof is expressly incorporated by reference herein.

Chitosan is represented by the general formula

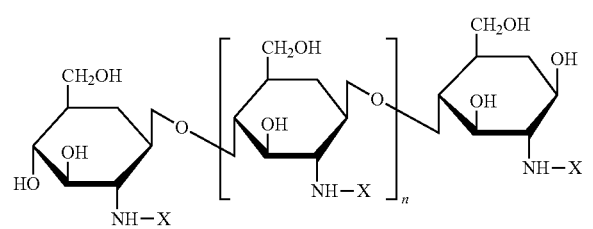

where n assumes values up to about 10,000, and X represents an acetyl radical or hydrogen. Chitosan is formed by the deacetylation and partial depolymerization (hydrolysis) of chitin, which may be represented by the structural formula

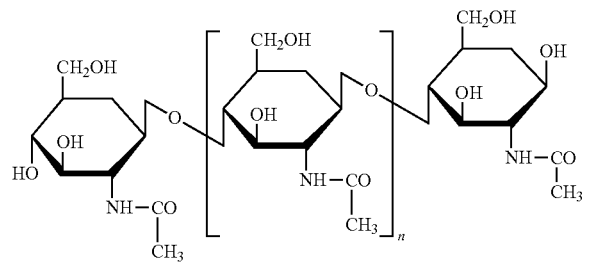

Chitin is an essential constituent of the exoskeleton [Greek: ο χιτων] of arthropods (e.g. insects, crabs, spiders) and may also be found in supporting tissues of other organisms (e.g. molluscs, algae and fungi).

In the range of about pH<6, chitosan is positively charged and there it is also soluble in aqueous systems. It is incompatible with anionic raw materials. Therefore, for the preparation of chitosan-containing oil-in-water emulsions, the use of nonionic emulsifiers is appropriate. Such emulsifiers are known per se, for example from EP-A 776 657, the entire disclosure whereof is expressly incorporated by reference herein.

Preferred chitosans for use in the invention are chitosans having a degree of deacetylation of >about 25%, in particular >about 55 to about 99% (determined by $^1$H-NMR).

It may also be advantageous to select chitosans having molecular weights between about 10,000 and about 1,000,000, in particular those having molecular weights between 100,000 and 1,000,000 (determined by means of gel permeation chromatography).

Polyacrylates are further examples of advantageous gelators for use in the present invention. Preferred polyacrylates according to the invention are acrylate-alkyl acrylate copolymers, in particular those from the group of so-called carbomers or Carbopols (Carbopol®, is a registered trademark of the B.F. Goodrich Company). Specifically, the acrylate-alkyl acrylate copolymers that are advantageous according to the invention are represented by the following structure:

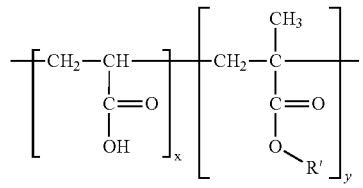

where R' represents a long-chain alkyl radical and x and y are numbers representing the stoichiometric ratio of the corresponding comonomers.

Particularly preferred in accordance with the invention are acrylate copolymers and/or acrylate-alkyl acrylate copolymers available from the B.F. Goodrich Company under the trade names Carbopol® 1382, Carbopol® 981 and Carbopol® 5984; and Carbopol® Ultrez.

Copolymers of $C_{10-30}$ alkyl acrylates and one or more monomers selected from acrylic acid, methacrylic acid and esters thereof, cross-linked with an allyl ether of saccharose and/or an allyl ether of pentaerythritol, are also advantageous for use in the present invention.

Compounds known under the INCI name "Acrylates/$C_{10-30}$ Alkyl Acrylate Crosspolymer" are advantageous. Particularly preferred are those available under the trade names Pemulen TR1 and Pemulen TR2 from the B.F. Goodrich Company.

In the finished cosmetic or dermatological preparations, the total amount of one or more hydrocolloids is advantageously less than 1.5% by weight, preferably between 0.1 and 1.0% by weight, based on the total weight of the preparations.

Advantageous according to the invention are ammonium acryloyldimethyltaurate/VP copolymers of the empirical formula $[C_7H_{16}N_2SO_4]_n$ $[C_6H_8NO]_m$, and a structure as follows:

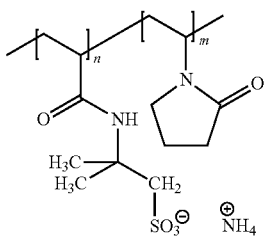

Preferred species for the purposes of the present invention have the Chemical Abstracts registration numbers 58374-69-9, 13162-05-5 and 88-12-0, and are available, e.g., under the trade name Aristoflex® AVC from Clariant GmbH, Germany.

Particular preference is given to copolymers of vinylpyrrolidone, for example the PVP hexadecene copolymer and the PVP eicosene copolymer, which are obtainable under the trade names Antaron V216 and Antaron V220 from GAF Chemicals Corporation, and Tricontayl PVP, and the like.

According to the invention it is very advantageous to use glycerin. Advantageously a preparation according to the invention contains from about 0.001% to about 30% by weight, in preferably from about 0.01% to about 15% by weight, particularly preferably from about 1% to about 7% by weight of glycerin, based on the total weight of the preparation.

The active ingredients used according to the invention can readily be incorporated into common cosmetic or dermatological formulations, advantageously into pump sprays, aerosol sprays, aerosol emulsion foams, creams, gels, ointments, tinctures, lotions, nail care products (e.g. nail polishes, nail polish removers, nail balsams) and the like.

It is also possible and in some instances advantageous to combine the active substance combinations used according to the invention with other active substances, for example with other antimicrobial, antimycotic or antiviral substances.

It is advantageous to buffer the compositions according to the invention. A pH range from about 3.5 to about 8.0 is advantageous. It is particularly favorable to choose the pH within a range of from about 6.5 to about 7.5.

The cosmetic and/or dermatological formulations of the present invention may have a conventional composition and can be used to treat the skin and/or the hair in terms of a dermatological treatment or a treatment in terms of cosmetic care. However, they can also be used in cosmetic products for decorative cosmetics.

For use, the cosmetic and dermatological formulations according to the invention may be applied to the skin and/or the hair in an adequate amount in the manner customary for cosmetics and dermatological products.

The cosmetic and dermatological preparations which are in the form of a sunscreen are advantageous. They may advantageously additionally comprise at least one UVA filter and/or at least one UVB filter and/or at least one inorganic pigment.

Cosmetic formulations according to the invention for the protection of the skin against UV rays can take various forms, as are, e.g., customarily used for this type of preparation. By way of non-limiting example, they can be present in the form of a solution, an emulsion of the water-in-oil (W/O) type or of the oil-in-water (O/W) type, or a multiple emulsion, for example of the water-in-oil-in-water (W/O/W) type, a gel, a hydrodispersion, a solid stick, or also an aerosol.

The cosmetic formulations according to the invention may comprise cosmetic auxiliaries as are customarily used in such preparations, e.g., preservatives, bactericides, antioxidants, perfumes, antifoams, dyes, coloring pigments, thickeners, surface-active substances, emulsifiers, emollients, moisturizers and/or humectants, fats, oils, waxes and other customary constituents of a cosmetic formulation, such as alcohols, polyols, polymers, foam stabilizers, electrolytes, organic solvents or silicone derivatives.

If the cosmetic or dermatological formulation is present in the form of a solution or lotion, non-limiting examples of solvents which may be used include:
  water or aqueous solutions;
  oils, such as triglycerides of capric or of caprylic acid, but preferably castor oil;
  fats, waxes and other natural and synthetic fatty substances, preferably esters of fatty acids with alcohols of low carbon number, e.g., with isopropanol, propylene glycol or glycerin, or esters of fatty alcohols with alkanoic acids of low carbon number or with fatty acids;
  alcohols, diols or polyols of low carbon number, and ethers thereof, preferably ethanol, isopropanol, propylene glycol, glycerin, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the above-mentioned solvents may be used. In the case of alcoholic solvents, water may be a further constituent.

According to the invention, favorable antioxidants which may be used include all antioxidants which are suitable or customary for cosmetic and/or dermatological applications.

The antioxidants are advantageously chosen from the group consisting of amino acids (for example, glycine, histidine, tyrosine, tryptophan) and derivatives thereof, imidazoles (for example, urocanic acid) and derivatives thereof, peptides, such as D,L-carnosine, D-carnosine, L-carnosine and derivatives thereof (for example, anserine), carotenoids, carotenes (for example, α-carotene, β-carotene, lycopene) and derivatives thereof, lipoic acid and derivatives thereof (for example, dihydrolipoic acid), aurothioglucose, propylthiouracil and other thiols (for example, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (for example, buthionine sulfoximines, homocysteine sulfoximine, buthionine sulfones, penta-, hexa- and heptathionine sulfoximine) in very low tolerated doses (for example, pmol to μmol/kg), and furthermore (metal) chelating agents (for example, α-hydroxy-fatty acids, palmitic acid, phytic acid, lactoferrin), α-hydroxy acids (for example, citric acid, lactic acid, malic acid), humic acid, bile acid, bile extracts, bilirubin, biliverdin, EDTA, EGTA and derivatives thereof, unsaturated fatty acids and derivatives thereof (for example, γ-linolenic acid, linoleic acid, oleic acid), licochalcones, licochalcone A (from radix glycyrrhizae inflatae), folic acid and derivatives thereof, ubiquinone and ubiquinol and derivatives thereof, vitamin C and derivatives (for example, ascorbyl palmitate, Mg ascorbyl phosphate, Na ascorbyl phosphate, ascorbyl acetate), tocopherols and derivatives (for example, vitamin E acetate), vitamin A and derivatives (vitamin A palmitate) and coniferyl benzoate of benzoin resin, rutic acid and derivatives thereof, isoflavones (isoflavone 150) and isoflavonoids, ferulic acid and derivatives thereof, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example, selenium methionine), stilbenes and derivatives thereof (for example, stilbene oxide, trans-stilbene oxide) and the derivatives of these active substances mentioned which are suitable according to the invention (salts, esters, ethers, sugars, nucleotides, nucleosides, peptides and lipids).

The amount of the antioxidants (one or more compounds) in the preparations is preferably from about 0.001% to about 30% by weight, particularly preferably from about 0.05% to about 20% by weight, in particular from about 1% to about 10% by weight, based on the total weight of the preparation.

The cosmetic preparations according to the invention may contain cosmetic auxiliaries, as are customarily used in such preparations, e.g., preservatives, bactericides, deodorants, antiperspirants, insect repellents, vitamins, antifoams, dyes, coloring pigments, thickeners, emollients, moisturizers and/or humectants, fats, oils, waxes and other customary constituents of a cosmetic formulation, such as alcohols, polyols, polymers, foam stabilizers, electrolytes, organic solvents or silicone derivatives.

Moreover, preparations according to the invention may advantageously comprise substances which absorb UV radiation in the UVB range, the total amount of filter substances being, for example, about 0.1% by weight to about 30% by weight, preferably about 0.5 to about 10% by weight, in particular about 1 to about 6% by weight, based on the total weight of the preparations, in order to provide cosmetic preparations that can protect the hair or the skin from the entire range of ultraviolet radiation. They can also be used as sunscreen for the hair.

Advantageous UVA filter substances for the purposes of the present invention include dibenzoylmethane derivatives, in particular 4-(tert-butyl)-4'-methoxydibenzoylmethane (CAS no. 70356-09-1) which is sold by Givaudan under the brand Parsol® 1789 and by Merck under the trade name Eusolex® 9020.

Advantageous other UV filter substances for the purposes of the present invention are sulfonated, water-soluble UV filters, such as e.g.
  phenylene-1,4-bis-(2-benzimidazyl)-3,3'-5,5'-tetrasulfonic acid and its salts, in particular the corresponding sodium, potassium or triethanolammonium salts, in particular phenylene-1,4-bis-(2-benzimidazyl-)-3,3'-5,5'-tetrasulfonic acid bis-sodium salt with the INCI name bisimidazylate (CAS no.: 180898-37-7), which is available, for example, under the trade name Neo Heliopan AP from Haarmann & Reimer;
  salts of 2-phenylbenzimidazole-5-sulfonic acid, such as its sodium, potassium or its triethanolammonium salt, and the sulfonic acid itself with the INCI name phenylbenzimidazole sulfonic acid (CAS no. 27503-81-7), which is available, for example, under the trade name Eusolex 232 from Merck or under the trade name Neo Heliopan Hydro from Haarmann & Reimer;
  1,4-di(2-oxo-10-sulfo-3-bornylidenemethyl)-benzene (also: 3,3'-(1,4-phenylenedimethylene)-bis-(7,7-dimethyl-2-oxo-bicyclo-[2.2.1]hept-1-ylmethane sulfonic acid) and salts thereof (in particular the corresponding 10-sulfato compounds, in particular the corresponding sodium, potassium or triethanolammonium salt), which is also known as benzene-1,4-di(2-oxo-3-bornylidenemethyl-10-sulfonic acid). Benzene-1,4-di(2-oxo-3-bornylidenemethyl-10-sulfonic acid) has the INCI name terephthalidene dicamphor sulfonic acid (CAS no.: 90457-82-2) and is available, for example, under the trade name Mexoryl SX from Chimex;
  sulfonic acid derivatives of 3-benzylidenecamphor, such as, e.g., 4-(2-oxo-3-bornylidenemethyl)benzenesulfonic acid, 2-methyl-5-(2-oxo-3-bornylidenemethyl)-sulfonic acid and salts thereof.

Advantageous UV filter substances for the purposes of the present invention include furthermore so-called broad-band filters, i.e., filter substances which absorb both UV-A and UV-B radiation.

Advantageous broad-band filters or UV-B filter substances are, for example, triazine derivatives, such as, e.g.
  2,4-bis-{[4-(2-ethylhexyloxy)-2-hydroxy]-phenyl}-6-(4-methoxyphenyl)-1,3,5-triazine (INCI: Aniso Triazine), which is available under the trade name Tinosorb® S from CIBA-Chemikalien GmbH;
  diethylhexylbutylamidotriazone (INCI: diethylhexylbutamidotriazone), which is available under the trade name UVASORB HEB from Sigma 3V;
  tris(2-ethylhexyl) 4,4',4"-(1,3,5-triazin-2,4,6-triyltriimino)-tris-benzoate, also: 2,4,6-tris-[anilino-(p-carbo-2'-ethyl-1'-hexyloxy)]-1,3,5-triazine (INCI: ethylhexyl triazone), which is sold by BASF Aktiengesellschaft under the trade name UVINUL® T 150.

Another advantageous broad-band filter for the purposes of the present invention is 2,2'-methylene-bis-(6-(2H-benzotriazol-2-yl)-4-(1,1,3,3-tetramethylbutyl)-phenol) which is obtainable under the trade name Tinosorb® M from CIBA-Chemikalien GmbH.

Another advantageous broad-band filter for the purposes of the present invention is 2-(2H-benzotriazol-2-yl)-4-methyl-6-[2-methyl-3-[1,3,3,3-tetramethyl-1-[(trimethylsilyl)oxy]disiloxanyl]propyl]-phenol (CAS no.: 155633-54-8) with the INCI name drometrizole trisiloxane, which is available under the trade name Mexoryl® XL from Chimex.

The further UV filter substances can be oil-soluble or water-soluble.

Advantageous oil-soluble UVB and/or broad-band filter substances for the purposes of the present invention are, e.g.:
  3-benzylidenecamphor derivatives, preferably 3-(4-methylbenzylidene)camphor, 3-benzylidenecamphor;
  4-aminobenzoic acid derivatives, preferably 2-ethylhexyl 4-(dimethylamino)-benzoate, amyl 4-(dimethylamino) benzoate;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  UV filters bonded to polymers;
  3-(4-(2,2-bis-ethoxycarbonylvinyl)-phenoxy)propenyl)-methoxysiloxane/dimethylsiloxane-copolymer which is available, e.g., under the trade name Parsol® SLX from Hoffmann La Roche.

Advantageous water-soluble filter substances are, e.g., sulfonic acid derivatives of 3-benzylidene camphor, such as, e.g., 4-(2-oxo-3-bornylidenemethyl)benzenesulfonic acid, 2-methyl-5-(2-oxo-3-bornylidenemethyl)sulfonic acid and salts thereof.

A further light protection filter substance which may advantageously be used according to the invention is ethylhexyl-2-cyano-3,3-diphenylacrylate(octocrylene), which is available from BASF under the name Uvinul® N 539.

Particularly advantageous preparations for the purposes of the present invention, which are characterized by a high or very high UVA and/or UVB protection furthermore preferably comprise, in addition to the filter substance(s) according to the invention, further UVA and/or broad-band filters, in particular dibenzoylmethane derivatives [for example, 4-(tert-butyl)-4'-methoxydibenzoylmethane], phenylene-1,4-bis(2-benzimidazyl)-3,3'-5,5'-tetrasulfonic acid and/or salts thereof, 1,4-di(2-oxo-10-sulfo-3-bornylidenemethyl)-benzene and/or salts thereof, and 2,4-bis-{[4-(2-ethylhexyloxy)-2-hydroxy]-phenyl}-6-(4-methoxyphenyl)-1,3,5-triazine, in each case individually or in any desired combinations with one another.

The list of UV filters mentioned which can be employed in the context of the present invention is of course not intended to be limiting.

The preparations according to the invention advantageously comprise the substances which absorb UV radiation in the UVA and/or UVB range in a total amount of, e.g., from about 0.1% to about 30 wt. %, preferably from about 0.5% to about 20 wt. %, in particular form about 1% to about 15 wt. %, in each case based on the total weight of the preparations, in order to provide cosmetic preparations which protect the hair or the skin from the entire range of ultraviolet radiation.

Particularly if crystalline or microcrystalline solids, e.g., inorganic micropigments, are to be incorporated in the preparations according to the invention the latter may also contain anionic, nonionic and/or amphoteric surfactants. Surfactants are amphiphilic substances that can dissolve organic, nonpolar substances in water.

The hydrophilic moieties of a surfactant molecule are mostly polar functional groups, for example —COO$^-$, —OSO$_3^-$, —SO$_3^-$, while the hydrophobic moieties are usually nonpolar hydrocarbon radicals. Surfactants are generally classified according to the type and charge of the hydrophilic molecular moiety. In this connection, it is possible to distinguish between four groups:

anionic surfactants, cationic surfactants, amphoteric surfactants and nonionic surfactants.

Anionic surfactants usually have as functional groups carboxylate, sulfate or sulfonate groups. In aqueous solution, they form negatively charged organic ions in acidic or neutral media. Cationic surfactants are characterized almost exclusively by the presence of a quaternary ammonium group. In aqueous solution they form positively charged organic ions in acidic or neutral media. Amphoteric surfactants contain both anionic and cationic groups and accordingly in aqueous solution behave like anionic or cationic surfactants, depending on the pH value. In strongly acidic media they have a positive charge, and in alkaline media they carry a negative charge. By contrast, in the neutral pH range, they are zwitterionic, as the example below serves to illustrate:

RNH$_2^+$CH$_2$CH$_2$COOH X$^-$ (at pH=2) X$^-$=any anion, e.g. Cl$^-$

RNH$_2^+$CH$_2$CH$_2$COO$^-$ (at pH=7)

RNHCH$_2$CH$_2$COO$^-$ B$^+$ (at pH=12) B$^+$=any cation, e.g., Na.$^+$

Polyether chains are typical of nonionic surfactants. Nonionic surfactants do not form ions in an aqueous medium.

A. Anionic Surfactants

Non-limiting examples of anionic surfactants which may be used advantageously include:

Acylamino acids (and salts thereof), such as
1. acyl glutamates, for example, sodium acyl glutamate, di-TEA-palmitoyl aspartate and sodium caprylic/capric glutamate,
2. acylpeptides, for example, palmitoyl-hydrolysed milk protein, sodium cocoyl-hydrolysed soy protein and sodium/potassium cocoyl-hydrolysed collagen,
3. sarcosinates, for example, myristoyl sarcosine, TEA-lauroyl sarcosinate, sodium lauroyl sarcosinate and sodium cocoyl sarcosinate,
4. taurates, for example sodium lauroyl taurate and sodium methylcocoyl taurate,
5. acyl lactylates, lauroyl lactylate, caproyl lactylate
6. alaninates Carboxylic acids and derivatives thereof, such as
1. carboxylic acids, for example, lauric acid, aluminum stearate, magnesium alkanolate and zinc undecylenate,
2. ester carboxylic acids, for example, calcium stearoyl lactylate, laureth-6 citrate and sodium PEG-4 lauramide carboxylate,
3. ether carboxylic acids, for example sodium laureth-13 carboxylate and sodium PEG-6 cocamide carboxylate.

Phosphoric esters and salts, such as, for example, DEA-oleth-10 phosphate and dilaureth-4 phosphate, Sulfonic acids and salts, such as
1. acyl isethionates, e.g., sodium/ammoniumcocoyl isethionate,
2. alkylarylsulfonates,
3. alkylsulfonates, for example, sodium cocomonoglyceride sulfate, sodium C$_{12-14}$-olefin sulfonate, sodium lauryl sulfoacetate and magnesium PEG-3 cocamide sulfate,
4. sulfosuccinates, for example dioctyl sodium sulfosuccinate, disodium laureth sulfosuccinate, disodium lauryl sulfosuccinate and disodium undecyleneamido-MEA sulfosuccinate, and Sulfuric esters, such as
1. alkyl ether sulfate, for example sodium, ammonium, magnesium, MIPA, TIPA laureth sulfate, sodium myreth sulfate and sodium C$_{12-13}$ pareth sulfate,
2. alkyl sulfates, for example sodium, ammonium and TEA lauryl sulfate.

B. Cationic Surfactants

Non-limiting examples of cationic surfactants which may be advantageously used include
1. alkylamines,
2. alkylimidazoles,
3. ethoxylated amines and
4. quaternary surfactants,
5. ester quats.

Quaternary surfactants contain at least one N atom which is covalently bonded to 4 alkyl or aryl groups. Irrespective of the pH value, this results in a positive charge. Alkylbetaine, alkylamidopropylbetaine and alkylamidopropylhydroxysulfaine are advantageous. The cationic surfactants which may be used according to the invention can also preferably be chosen from quaternary ammonium compounds, in particular benzyltrialkylammonium chlorides or bromides, such as, for example, benzyldimethylstearylammonium chloride, and also alkyltrialkylammonium salts, for example, cetyltrimethylammonium chloride or bromide, alkyldimethylhydroxyethylammonium chlorides or bromides, dialkyldimethylammonium chlorides or bromides, alkylamidoethyltrimethylammonium ether sulfates, alkylpyridinium salts, for example, lauryl- or cetylpyridinium chloride, imidazoline derivatives and compounds having cationic character, such as amine oxides, for example, alkyldimethylamine oxides or alkylaminoethyldimethylamine oxides. In particular the use of cetyltrimethylammonium salts is advantageous.

C. Amphoteric Surfactants

Non-limiting examples of amphoteric surfactants which may be used advantageously include
1. acyl/dialkylethylenediamine, for example, sodium acyl amphoacetate, disodium acyl amphodipropionate, disodium alkyl amphodiacetate, sodium acyl amphohydroxypropylsufonate, disodium acyl amphodiacetate and sodium acyl amphopropionate,
2. N-alkylamino acids, for example, aminopropylalkylglutamide, alkylaminopropionic acid, sodium alkylimidodipropionate and lauroamphocarboxyglycinate.

D. Nonionic Surfactants

Non-limiting examples of nonionic surfactants which can be used advantageously are
1. alcohols,
2. alkanolamides, such as cocamides MEA/DEA/MIPA,
3. amine oxides, such as cocoamidopropylamine oxide,
4. esters which are formed by esterification of carboxylic acids with ethylene oxide, glycerin, sorbitol or other alcohols,
5. ethers, for example ethoxylated/propoxylated alcohols, ethoxylated/propoxylated esters, ethoxylated/propoxylated glycerin esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside.
6. sucrose esters, sucrose ethers
7. polyglycerol esters, diglycerol esters, monoglycerol esters
8. methylglucose esters, esters of hydroxy acids Also advantageous is the use of a combination of anionic and/or amphoteric surfactants with one or more nonionic surfactants.

The surface-active substance may be present in the preparations according to the invention in a concentration of, for example, from about 1% to about 95% by weight, based on the total weight of the preparation.

The lipid phase of the cosmetic or dermatological emulsions according to the present invention may advantageously be chosen from the following substances:
mineral oils, mineral waxes;
oils, such as triglycerides of capric or of caprylic acid, and also natural oils, such as, for example, castor oil;
fats, waxes and other natural and synthetic fatty substances, preferably esters of fatty acids with alcohols of low carbon number, e.g. with isopropanol, propylene glycol or glycerin, or esters of fatty alcohols with alkanoic acids of low carbon number or with fatty acids;
alkyl benzoates;
silicone oils, such as dimethylpolysiloxanes, diethylpolysiloxanes, diphenylpolysiloxanes, and mixed forms thereof.

The oil phase of the emulsions of the present invention may advantageously be chosen from esters of saturated and/or unsaturated, branched and/or unbranched alkanecarboxylic acids having a chain length of from about 3 to about 30 carbon atoms and saturated and/or unsaturated, branched and/or unbranched alcohols having a chain length of from about 3 to about 30 carbon atoms and from esters of aromatic carboxylic acids and saturated and/or unsaturated, branched and/or unbranched alcohols having a chain length of from about 3 to about 30 carbon atoms. Such ester oils can advantageously be chosen from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g., jojoba oil.

The oil phase may also advantageously be chosen from branched and unbranched hydrocarbons and hydrocarbon waxes, silicone oils, dialkyl ethers, saturated or unsaturated, branched or unbranched alcohols, and fatty acid triglycerides, namely the triglycerol esters of saturated and/or unsaturated, branched and/or unbranched alkanecarboxylic acids having a chain length of from about 8 to about 24 carbon atoms, in particular from about 12 to about 18 carbon atoms. The fatty acid triglycerides can, for example, be advantageously chosen from synthetic, semisynthetic and natural oils, e.g., olive oil, sunflower oil, soy oil, peanut oil, rapeseed oil, almond oil, palm oil, coconut oil, palm kernel oil and the like.

Any mixtures of such oil and wax components can also be used advantageously for the purposes of the present invention. In some instances, it may also be advantageous to use waxes, for example cetyl palmitate, as the sole lipid component of the oil phase.

The oil phase may advantageously be chosen from 2-ethylhexyl isostearate, octyldodecanol, isotridecyl isononanoate, isoeicosane, 2-ethylhexyl cocoate, $C_{12-15}$-alkyl benzoate, caprylic/capric triglyceride, and dicaprylyl ether.

Particularly advantageous mixtures are those of $C_{12-15}$-alkyl benzoate and 2-ethylhexyl isostearate, those of $C_{12-15}$-alkyl benzoate and isotridecyl isononanoate, and those of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Advantageously, the oil phase may also have a content of cyclic or linear silicone oils, or consist entirely of such oils, although it is preferred to use an additional content of other oil phase components apart from the silicone oil or the silicone oils.

Cyclomethicone (e.g., decamethylcyclopentasiloxane) may advantageously be chosen as the silicone oil for use in the present invention. However, other silicone oils can also be used advantageously for the purposes of the present invention, for example undecamethylcyclotrisiloxane, polydimethylsiloxane, and poly(methylphenylsiloxane).

Mixtures of cyclomethicone and isotridecyl isononanoate, and of cyclomethicone and 2-ethylhexyl isostearate are also particularly advantageous.

The aqueous phase of the preparations according to the invention optionally advantageously comprises alcohols, diols or polyols of low carbon number, and ethers thereof, preferably ethanol, isopropanol, propylene glycol, glycerin, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, and glycerin.

Preparations according to the invention which are present in the form of emulsions contain one or more emulsifiers. O/W emulsifiers may advantageously be chosen, for example, from the group of polyethoxylated, polypropoxylated or polyethoxylated and polypropoxylated products, e.g.:

fatty alcohol ethoxylates,
ethoxylated wool wax alcohols,
polyethylene glycol ethers of the general formula $$R-O-(-CH_2-CH_2-O-)_n-R',$$

fatty acid ethoxylates of the general formula $$R-COO-(-CH_2-CH_2-O-)_n-H,$$

etherified fatty acid ethoxylates of the general formula $$R-COO-(-CH_2-CH_2-O-)_n-R',$$

esterified fatty acid ethoxylates of the general formula $$R-COO-(-CH_2-CH_2-O-)_n-C(O)-R',$$

polyethylene glycol glycerol fatty acid esters,
ethoxylated sorbitan esters,
cholesterol ethoxylates,
ethoxylated triglycerides,
alkyl ether carboxylic acids of the general formula $$R-O-(-CH_2-CH_2-O-)_n-CH_2-COOH$$

wherein n is a number of from about 5 to about 30,
polyoxyethylene sorbitol fatty acid esters,
alkyl ether sulfates of the general formula $$R-O-(-CH_2-CH_2-O-)_n-SO_3-H,$$

fatty alcohol propoxylates of the general formula $$R-O-(-CH_2-CH(CH_3)-O-)_n-H,$$

polypropylene glycol ethers of the general formula $$R-O-(-CH_2-CH(CH_3)-O-)_n-R',$$

propoxylated wool wax alcohols,
etherified fatty acid propoxylates $$R-COO-(-CH_2-CH(CH_3)-O-)_n-R',$$

esterified fatty acid propoxylates of the general formula $$R-COO-(-CH_2-CH(CH_3)-O-)_n-C(O)-R',$$

fatty acid propoxylates of the general formula $$R-COO-(-CH_2-CH(CH_3)-O-)_n-H,$$

polypropylene glycol glycerol fatty acid esters,
propoxylated sorbitan esters,
cholesterol propoxylates,
propoxylated triglycerides,
alkyl ether carboxylic acids of the general formula $$R-O-(-CH_2-CH(CH_3)O-)_n-CH_2-COOH,$$

alkyl ether sulfates or the parent acids of these sulfates of the general formula $$R-O-(-CH_2-CH(CH_3)-O-)_n-SO_3-H,$$

fatty alcohol ethoxylates/propoxylates of the general formula $$R-O-X_n-Y_m-H,$$

polypropylene glycol ethers of the general formula $$R-O-X_n-Y_m-R',$$

etherified fatty acid propoxylates of the general formula $$R-COO-X_n-Y_m-R',$$

fatty acid ethoxylates/propoxylates of the general formula $$R-COO-X_n-Y_m-H.$$

According to the invention, the polyethoxylated or polypropoxylated or polyethoxylated and polypropoxylated O/W emulsifiers used are particularly advantageously chosen from the group of substances having HLB values of from about 11 to about 18, very particularly advantageously having HLB values of from about 14.5 to about 15.5, provided the O/W emulsifiers have saturated radicals R and R'. If the O/W emulsifiers have unsaturated radicals R and/or R', or isoalkyl derivatives are present, the preferred HLB values of such emulsifiers may also be lower or higher.

It is advantageous to choose the fatty alcohol ethoxylates from ethoxylated stearyl alcohols, cetyl alcohols, cetylstearyl alcohols (cetearyl alcohols). Particular preference is given to:

polyethylene glycol(13) stearyl ether (steareth-13), polyethylene glycol(14) stearyl ether (steareth-14), polyethylene glycol(15) stearyl ether (steareth-15), polyethylene glycol(16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20), polyethylene glycol(12) isostearyl ether (isosteareth-12), polyethylene glycol (13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20), polyethylene glycol(13) cetyl ether (ceteth-13), polyethylene glycol(14) cetyl ether (ceteth-14), polyethylene glycol(15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20), polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20), polyethylene glycol(12)oleyl ether (oleth-12), polyethylene glycol(13)oleyl ether (oleth-13), polyethylene glycol(14)oleyl ether (oleth-14), polyethylene glycol(15) oleyl ether (oleth-15), polyethylene glycol(12)lauryl ether (laureth-12), polyethylene glycol(12)isolauryl ether (isolaureth-12), polyethylene glycol(13)cetylstearyl ether (ceteareth-13), polyethylene glycol(14)cetylstearyl ether (ceteareth-14), polyethylene glycol(15)cetylstearyl ether (ceteareth-15), polyethylene glycol(16)cetylstearyl ether (ceteareth-16), polyethylene glycol(17)cetylstearyl ether (ceteareth-17), polyethylene glycol(18)cetylstearyl ether (ceteareth-18), polyethylene glycol(19) cetylstearyl ether (ceteareth-19), polyethylene glycol(20)cetylstearyl ether (ceteareth-20).

It may also be advantageous to choose the fatty acid ethoxylates from the following:

polyethylene glycol(20)stearate, polyethylene glycol(21)stearate, polyethylene glycol(22)stearate, polyethylene glycol(23)stearate, polyethylene glycol(24)stearate, polyethylene glycol(25)stearate, polyethylene glycol(12)isostearate, polyethylene glycol(13)isostearate, polyethylene glycol(14)isostearate, polyethylene glycol(15)isostearate, polyethylene glycol(16)isostearate, polyethylene glycol(17)isostearate, polyethylene glycol(18)isostearate, polyethylene glycol(19)isostearate, polyethylene glycol(20)isostearate, polyethylene glycol(21)isostearate, polyethylene glycol(22)isostearate, polyethylene glycol(23)isostearate, polyethylene glycol(24)isostearate, polyethylene glycol(25)isostearate, polyethylene glycol(12)oleate, polyethylene glycol(13)oleate, polyethylene glycol(14)oleate, polyethylene glycol(15)oleate, polyethylene glycol(16)oleate, polyethylene glycol(17)oleate, polyethylene glycol(18)oleate, polyethylene glycol(19)oleate, polyethylene glycol(20)oleate.

Sodium laureth-11 carboxylate may advantageously be used as the ethoxylated alkyl ether carboxylic acid or salt thereof.

Sodium laureth-1-4 sulfate may advantageously be used as alkyl ether sulfate.

Polyethylene glycol(30) cholesteryl ether may advantageously be used as ethoxylated cholesterol derivative. Polyethylene glycol(25)soyasterol has also proven beneficial.

The polyethylene glycol(60) evening primrose glycerides can advantageously be used as ethoxylated triglycerides.

It may also be advantageous to choose the polyethylene glycol glycerin fatty acid esters from polyethylene glycol (20)glyceryl laurate, polyethylene glycol(21)glyceryl laurate, polyethylene glycol(22)glyceryl laurate, polyethylene glycol(23)glyceryl laurate, polyethylene glycol(6)glyceryl caprate/caprinate, polyethylene glycol(20)glyceryl oleate, polyethylene glycol(20)glyceryl isostearate, polyethylene glycol(18)glyceryl oleate/cocoate.

It may likewise be favorable to choose the sorbitan esters from polyethylene glycol(20)sorbitan monolaurate, polyethylene glycol(20)sorbitan monostearate, polyethylene glycol (20)sorbitan monoisostearate, polyethylene glycol(20)sorbitan monopalmitate, polyethylene glycol(20)sorbitan monooleate.

Non-limiting examples of advantageous W/O emulsifiers which may be used include: fatty alcohols having from about 8 to about 30 carbon atoms, monoglycerol esters of saturated and/or unsaturated, branched and/or unbranched alkanecarboxylic acids having a chain length of from about 8 to about 24, in particular from about 12 to about 18 carbon atoms, diglycerol esters of saturated and/or unsaturated, branched and/or unbranched alkanecarboxylic acids having a chain length of from about 8 to about 24, in particular from about 12 to about 18 carbon atoms, monoglycerol ethers of saturated and/or unsaturated, branched and/or unbranched alcohols having a chain length of from about 8 to about 24, in particular from about 12 to about 18 carbon atoms, diglycerol ethers of saturated and/or unsaturated, branched and/or unbranched alcohols having a chain length of from about 8 to about 24, in particular from about 12 to about 18 carbon atoms, propylene glycol esters of saturated and/or unsaturated, branched and/or unbranched alkanecarboxylic acids having a chain length of from about 8 to about 24, in particular from about 12 to about 18 carbon atoms, and sorbitan esters of saturated and/or unsaturated, branched and/or unbranched alkanecarboxylic acids having a chain length of from about 8 to about 24, in particular from about 12 to about 18 carbon atoms.

Particularly advantageous W/O emulsifiers comprise glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2)stearyl ether(steareth-2), glyceryl monolaurate, glyceryl monocaprinate, glyceryl monocaprylate.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

| Example 1 - O/W emulsion | % by weight |
|---|---|
| Glyceryl stearate citrate | 2.0 |
| Myristyl myristate | 1.0 |
| Stearyl alcohol | 2.0 |
| Cetyl alcohol | 1.0 |
| Hydrogenated coco glycerides | 2.0 |
| Butyleneglycol dicaprylate/dicaprate | 1.0 |
| Ethylhexyl palmic acid ester | 3.0 |
| Vaseline | 1.0 |
| Dicaprylyl ether | 3.0 |
| $TiO_2$ | 1.0 |
| Ethylhexyl methoxycinnamate | 2.0 |
| Ubiquinone (Q10) | 0.03 |
| Creatinine | 0.1 |
| Creatine | 1.0 |
| Phenoxyethanol | 0.8 |
| p-Hydroxybenzoic acid alkyl ester (paraben) | 0.4 |
| Cyclodextrin | 0.4 |
| Polyacrylic acid (carbomer) | 0.1 |
| Ammoniumacryloyldimethyltaurate/vinylpyrrolidone copolymers | 0.4 |
| Glycerin | 15 |
| Water-soluble and/or oil-soluble dyes | 0.05 |
| Fillers/additives (distarch phosphate, $SiO_2$, BHT, talc, aluminum stearate) | 0.1 |
| Perfume | q.s. |
| Water | ad 100 |

| Example 2 - O/W emulsion | % by weight |
|---|---|
| Glyceryl stearate, self-emulsifying | 5.0 |
| Stearyl alcohol | 1.0 |
| Shea butter | 1.0 |
| $C_{12-15}$ alkylbenzoate | 3.0 |

Example 2 - O/W emulsion

| Ingredient | % by weight |
|---|---|
| Caprylic acid/capric acid triglycerides | 1.0 |
| Mineral oil | 1.0 |
| Dicaprylyl carbonate | 3.0 |
| Ethylhexyl methoxycinnamate | 3.0 |
| Ethylhexyltriazone | 1.0 |
| Bis-ethylhexyloxyphenol-methoxyphenyl triazine | 1.0 |
| Citric acid, sodium salt | 0.1 |
| Creatine | 0.5 |
| Allantoin | 0.3 |
| Niacinamide | 0.2 |
| Phenoxyethanol | 0.5 |
| p-Hydroxybenzoic acid alkyl ester (paraben) | 0.3 |
| Hexamidindiisethionate | 0.04 |
| 1,3-Dimethylol-5,5-dimethyl-hydantoin(DMDM hydantoin) | 0.1 |
| Ammoniumacryloyldimethyltaurate/vinylpyrrolidone copolymers | 0.5 |
| Glycerin | 10.0 |
| Butylene glycol | 1.0 |
| Fillers/additives (SiO$_2$, BHT, microcellulose) | 1.0 |
| Perfume | q.s. |
| Water | ad 100 |

Example 3 - O/W emulsion

| Ingredient | % by weight |
|---|---|
| Glyceryl stearate | 3.0 |
| PEG-40-stearate | 1.0 |
| Cetyl alcohol | 3.0 |
| Shea butter | 2.0 |
| C$_{12-15}$ Alkylbenzoate | 2.0 |
| Caprylic acid/capric acid triglyceride | 2.0 |
| Octyldodecanol | 1.0 |
| Vaseline | 1.0 |
| Cyclomethicon | 4.0 |
| Dimethicone | 1.0 |
| Dicaprylylether | 2.0 |
| TiO$_2$ | 1.0 |
| Ethylhexyl methoxycinnamate | 5.0 |
| Diethylhexyl butamidotriazone | 1.0 |
| Bis-ethylhexyloxyphenol-methoxyphenyltriazine | 2.0 |
| Ubiquinone (Q10) | 0.1 |
| Tocopherylacetate | 1.0 |
| Creatine | 0.5 |
| Retinyl palmitate | 0.1 |
| Ethylenediamine tetraacetic acid (sodium salt) | 0.2 |
| Phenoxyethanol | 0.3 |
| p-Hydroxybenzoic acid alkyl ester (paraben) | 0.2 |
| Hydroxypropylmethylcellulose | 0.3 |
| Ammoniumacryloyldimethyltaurate/vinylpyrrolidone copolymers | 0.3 |
| Glycerin | 7.0 |
| Fillers/additives (SiO$_2$, BHT, talc, dye) | 0.2 |
| Perfume | q.s. |
| Water | ad 100 |

Example 4 - O/W emulsion

| Ingredient | % by weight |
|---|---|
| Glyceryl stearate | 1.0 |
| Stearic acid | 4.0 |
| Stearyl alcohol | 1.0 |
| Cetyl alcohol | 3.0 |
| Butylene glycol dicaprylate/dicaprate | 1.0 |
| Caprylic acid/capric acid triglyceride | 2.0 |
| Jojoba oil | 1.0 |
| Dimethicone | 1.0 |
| Dicaprylylcarbonate | 3.0 |
| TiO$_2$ | 1.0 |
| Ethylhexyl methoxycinnamate | 7.5 |
| Bis-ethylhexyloxyphenol-methoxyphenyltriazine | 2.0 |
| Phenylbenzimidazole sulfonic acid | 2.0 |
| Retinyl palmitate | 0.1 |
| Creatine | 0.8 |
| Phenoxyethanol | 0.2 |
| p-hydroxy benzoic acid alkylester (paraben) | 0.3 |
| Iodopropynylbutylcarbamate | 0.02 |
| PVP hexadecene copolymer | 0.3 |
| Carrageenan | 0.3 |
| Glycerin | 5.0 |
| Methylpropanediol | 2.0 |
| Fillers/additives (SiO$_2$, BHT, talc, mica) | 1.0 |
| Perfume | q.s. |
| Water | ad 100 |

Example 5 - O/W emulsion

| Ingredient | % by weight |
|---|---|
| Glyceryl stearate | 2.0 |
| PEG-40-stearate | 1.0 |
| Myristyl myristate | 1.0 |
| Cetearyl alcohol | 2.0 |
| Shea butter | 2.0 |
| C$_{12-15}$ Alkylbenzoate | 3.0 |
| Caprylic acid/capric acid triglyceride | 2.0 |
| Ethylhexyl palmic acid ester | 1.0 |
| Vaseline | 2.0 |
| Cyclomethicone | 5.0 |
| TiO$_2$ | 1.0 |
| Ethylhexylmethoxycinnamate | 5.0 |
| 2-hydroxy-4-methoxy-benzophenone (oxybenzone) | 3.0 |
| Phenylbenzimidazole sulfonic acid | 2.0 |
| Ubiquinone (Q10) | 0.05 |
| Tocopherylacetate | 0.5 |
| Creatinine | 0.2 |
| Creatine | 1.0 |
| EDTA | 0.2 |
| Sodium ascorbylphosphate | 0.1 |
| Phenoxyethanol | 0.2 |
| p-hydroxy benzoic acid alkylester (paraben) | 0.3 |
| Carbopol 981 (polyacrylic acid, carbomer) | 0.2 |
| Aluminum starch octenylsuccinate | 1.0 |
| Glycerin | 5.0 |
| Fillers/additives (ZnO, nylon microparticles, SiO$_2$) | 2.0 |
| Perfume | q.s. |
| Water | ad 100 |

Example 6 - O/W emulsion

| Ingredient | % by weight |
|---|---|
| Cetyl alcohol | 2.0 |
| Shea butter | 1.0 |
| Caprylic acid/capric acid triglyceride | 2.0 |
| Octyldodecanol | 1.0 |
| Dicaprylylcarbonate | 5.0 |
| Dimethylpolysiloxane (dimethicone) | 1.0 |
| Polydecene | 2.0 |
| Creatine | 1.0 |
| Ethylhexylmethoxycinnamate | 3.0 |
| Bis-ethylhexyloxyphenol-methoxyphenyltriazine | 1.0 |
| Sodium ascorbylphosphate | 0.05 |
| Iminodisuccinate | 0.2 |
| Ubiquinone | 0.05 |
| Phenoxyethanol | 0.3 |
| p-Hydroxybenzoic acid alkyl ester (paraben) | 0.4 |
| Alkylacrylate crosspolymer | 0.2 |
| Carrageenan | 0.2 |
| Glycerin | 5.0 |
| Perfume | q.s. |
| Water | ad 100 |

| Example 7 - O/W emulsion | % by weight |
|---|---|
| Glyceryl stearate | 2.5 |
| PEG-40-stearate | 1.0 |
| Cetearyl alcohol | 2.0 |
| Hydrogenated coco glycerides | 1.0 |
| Shea butter | 2.0 |
| $C_{12-15}$ alkylbenzoate | 4.0 |
| Caprylic acid/capric acid triglyceride | 2.0 |
| Octyldodecanol | 1.0 |
| Vaseline | 1.0 |
| Dicaprylylcarbonate | 3.0 |
| $TiO_2$ | 1.0 |
| Ethylhexyl cyanodiphenylacrylate (octocrylene) | 5.0 |
| Phenylbenzimidazole sulfonic acid | 1.0 |
| Butylmethoxy dibenzoylmethane | 2.0 |
| Niacinamide | 0.1 |
| Retinyl palmitate | 0.1 |
| Creatinine | 0.02 |
| Creatine | 0.2 |
| Cyclodextrin | 0.2 |
| Iminodisuccinate | 0.2 |
| Phenoxyethanol | 0.5 |
| p-Hydroxybenzoic acid alkyl ester (paraben) | 0.4 |
| Iodopropynylbutylcarbamate | 0.05 |
| 2-Ethylhexyl glycerin ether (octoxyglycerin) | 0.5 |
| Carbopol 980 (polyacrylic acid, Carbomer) | 0.2 |
| Xanthan gum | 0.1 |
| Nylon microparticles | 1.0 |
| Glycerin | 10.0 |
| Additives (distarch phosphate, talc, BHT) | 0.03 |
| Perfume | q.s. |
| Water | ad 100 |

| Example 8 - O/W emulsion | % by weight |
|---|---|
| Polyglyceryl-3-methylglucosedistearate | 3.0 |
| Sorbitan stearate | 1.0 |
| Behenyl alcohol | 2.0 |
| Cetyl alcohol | 1.0 |
| $C_{12-15}$ Alkylbenzoate | 2.0 |
| Butyleneglycol dicaprylate/dicaprate | 2.0 |
| Caprylic acid/capric acid triglyceride | 2.0 |
| Hydrogenated polydecene | 1.0 |
| Dimethylpolysiloxane (dimethicone) | 1.0 |
| Dicaprylyl carbonate | 2.0 |
| Ethylhexyl methoxycinnamate | 5.0 |
| Butylmethoxy dibenzoylmethane | 2.0 |
| Phenylbenzimidazole sulfonic acid | 1.0 |
| Creatine | 0.3 |
| Tocopheryl acetate | 0.5 |
| Ethylenediamine tetraacetic acid | 0.2 |
| Phenoxyethanol | 0.4 |
| p-Hydroxybenzoic acid alkyl ester (paraben) | 0.4 |
| Ethanol denatured | 3.0 |
| Xanthan gum | 0.2 |
| Ammoniumacryloyldimethyltaurate/vinylpyrrolidone copolymer | 0.3 |
| Glycerin | 4.5 |
| Additives ($SiO_2$, talc) | 0.5 |
| Perfume | q.s. |
| Water | ad 100 |

| Example 9 O/W emulsion | % by weight |
|---|---|
| Cetearyl glucoside | 2.0 |
| Myristyl myristate | 1.0 |
| Stearyl alcohol | 4.0 |
| $C_{12-15}$ Alkylbenzoate | 2.0 |
| Caprylic acid/capric acid triglyceride | 3.0 |
| Hydrogenated polydecene | 1.0 |
| Dicaprylyl carbonate | 3.0 |
| Polydecene | 4.0 |
| Ethylhexyl methoxycinnamate | 3.0 |
| Ethylhexyl cyanodiphenylacrylate (octocrylene) | 3.0 |
| Butylmethoxy dibenzoylmethane | 1.0 |
| Creatine | 1.5 |
| Tocopherylacetate | 1.0 |
| Trisodium EDTA | 0.1 |
| Phenoxyethanol | 0.7 |
| p-Hydroxybenzoic acid alkyl ester (paraben) | 0.4 |
| 2-Ethylhexyl glycerin ether (octoxyglycerin) | 0.4 |
| Ammoniumpolyacryloyldimethyltaurate | 0.3 |
| Aluminum starch octenylsuccinate | 1.0 |
| Glycerin | 4.0 |
| Butyleneglycol | 2.0 |
| Additives (distarch phosphate, $SiO_2$, talc, aluminum stearate) | 3.0 |
| Perfume | q.s. |
| Water | ad 100 |

| Example 10 O/W emulsion | % by weight |
|---|---|
| Glyceryl stearate | 1.0 |
| Stearic acid | 2.5 |
| Behenyl alcohol | 2.0 |
| Cetyl alcohol | 3.0 |
| Hydrogenated cocoglycerides | 1.0 |
| $C_{12-15}$ alkylbenzoate | 2.0 |
| Octyldodecanol | 2.0 |
| Octamethyltetrasiloxane (cyclomethicone) | 2.0 |
| Dimethylpolysiloxane (dimethicone) | 1.0 |
| Dicaprylyl carbonate | 4.0 |
| $TiO_2$ | 1.0 |
| Ethylhexyl methoxycinnamate | 3.0 |
| Ubiquinone (Q10) | 0.05 |
| Bisabolol | 0.1 |
| Creatine | 0.2 |
| Tocopheryl acetate | 0.5 |
| Iminodisuccinate | 0.1 |
| Phenoxyethanol | 0.3 |
| p-Hydroxybenzoic acid alkyl ester (paraben) | 0.4 |
| Ethanol denatured | 3.0 |
| Carrageenan (*chondrus crispus*) | 0.2 |
| Glycerin | 7.0 |
| Additives (distarch phosphate, talc, BHT) | 1.0 |
| Perfume | q.s. |
| Water | ad 100 |

| Example 11 O/W emulsion | % by weight |
|---|---|
| Polyethyleneglycol(21)stearyl-ether (steareth-21) | 2.0 |
| Polyethyleneglycol(2)stearyl-ether (steareth-2) | 1.0 |
| Cetearyl alcohol | 2.0 |
| Shea butter | 1.0 |
| $C_{12-15}$ Alkylbenzoate | 5.0 |
| Octyldodecanol | 1.0 |
| Mineral oil | 1.0 |
| Octamethyltetrasiloxane (cyclomethicone) | 2.0 |
| Dicaprylyl ether | 2.0 |
| $TiO_2$ | 1.0 |
| Ethylhexyl methoxycinnamate | 4.0 |
| Ethylhexyltriazone | 1.0 |
| Ubiquinone (Q10) | 0.02 |
| Creatinine | 0.1 |
| Creatine | 1.0 |
| Biotin | 0.03 |
| Phenoxyethanol | 0.5 |
| p-Hydroxybenzoic acid alkyl ester (paraben) | 0.3 |
| Iodopropynylbutylcarbamate | 0.1 |
| Carbopol 980 (polyacrylic acid, carbomer) | 0.2 |
| Ammoniumacryloyldimethyltaurate/vinylpyrrolidone copolymers | 0.3 |
| Glycerin | 6.0 |
| Additives (distarch phosphate, BHT, dye) | 0.5 |

| Example 11 O/W emulsion | % by weight |
|---|---|
| Perfume | q.s. |
| Water | ad 100 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological preparation, wherein the preparation comprises
   (a) from about 0.001% to about 10% by weight of at least one of creatine and a creatine compound,
   (b) from about 0.001% to about 10% by weight of creatinine, and
   (c) at least about 0.1% by weight of one or more hydrocolloids,
   and wherein the preparation is present as a hydrodispersion.

2. The preparation of claim 1, wherein (a) comprises one or more of creatine, creatine phosphate, creatine sulfate, creatine acetate, creatine ascorbate, and an ester of creatine with a mono- or polyfunctional alcohol.

3. The preparation of claim 2, wherein the preparation comprises from about 0.01% to about 1% by weight of (a).

4. The preparation of claim 1, wherein the preparation comprises from about 0.01% to about 1% by weight of (b).

5. The preparation of claim 3, wherein the preparation comprises from about 0.01% to about 1% by weight of (b).

6. The preparation of claim 1, wherein the preparation further comprises from about 0.001% to about 30% by weight of glycerin.

7. The preparation of claim 4, wherein the preparation further comprises from about 0.01% to about 15% by weight of glycerin.

8. The preparation of claim 1, wherein the preparation further comprises from about 1% to about 7% by weight of glycerin.

9. The preparation of claim 5, wherein the preparation further comprises from about 1% to about 7% by weight of glycerin.

10. The preparation of claim 5, wherein a weight ratio of creatinine to creatine is from about 10:1 to about 1:10.

11. The preparation of claim 10, wherein the weight ratio is from about 4:1 to about 3:7.

12. The preparation of claim 10, wherein the weight ratio is from about 2:1 to about 1:2.

13. The preparation of claim 1, wherein the preparation comprises less than about 1.5% by weight of the one or more hydrocolloids.

14. The preparation of claim 5, wherein the preparation comprises not more than about 1.0% by weight of the one or more hydrocolloids.

15. The preparation of claim 13, wherein the one or more hydrocolloids comprise at least one of
   a) organic, fully synthetic compounds of polyacrylic acids,
   b) copolymers and crosspolymers of polyacrylic acid derivatives
   c) ammonium dimethyltauramide/vinylformamide copolymer
   d) copolymers/crosspolymers comprising acryloyldimethyltaurate
   e) hydrophilic gums and hydrophilic derivatives thereof
   f) cellulose, cellulose derivatives and microcrystalline cellulose.

16. The preparation of claim 1, wherein the one or more hydrocolloids comprise one or more of agar agar, alginate, pectin, guar flour, dextrin, casein.

17. The preparation of claim 15, wherein the one or more hydrocolloids comprise copolymers/crosspolymers comprising acryloyldimethyltaurate.

18. The preparation of claim 1, wherein the one or more hydrocolloids comprise ammonium dimethyltauramide/vinylformamide copolymer.

19. The preparation of claim 15, wherein the one or more hydrocolloids comprise ammonium dimethyltauramide/vinylformamide copolymer.

20. The preparation of claim 15, wherein the one or more hydrocolloids comprise microcrystalline cellulose.

21. The preparation of claim 15, wherein the one or more hydrocolloids comprise carrageen.

22. The preparation of claim 12, wherein the one or more hydrocolloids comprise ammonium dimethyltauramide/vinylformamide copolymer.

23. The preparation of claim 1, wherein an aqueous phase of the hydrodispersion has a pH value of from about 6.0 to about 8.0.

24. The preparation of claim 23, wherein the pH value is from about 6.2 to about 7.8.

25. The preparation of claim 23, wherein the pH value is from about 6.5 to about 7.5.

26. The preparation of claim 1, wherein the one or more hydrocolloids comprise ammonium dimethyltauramide/vinylformamide copolymer.

27. The preparation of claim 1, wherein the preparation further comprises one or more UV filter substances.

28. The preparation of claim 1, wherein the preparation comprises less than about 1.5% by weight of the one or more hydrocolloids.

29. A cosmetic or dermatological preparation, wherein the preparation comprises creatinine, at least one compound selected from creatine, creatine phosphate, creatine sulfate, creatine acetate, creatine ascorbate, and esters of creatine with a mono- or polyfunctional alcohol, and not more than about 1.5% by weight of one or more hydrocolloids selected from:
   a) organic, fully synthetic compounds of polyacrylic acids,
   b) copolymers and crosspolymers of polyacrylic acid derivatives
   c) ammonium dimethyltauramide/vinylformamide copolymer
   d) copolymers/crosspolymers comprising acryloyldimethyltaurate
   e) cellulose, cellulose derivatives and microcrystalline cellulose;

a weight ratio of creatinine to creatine being from 10:1 to 1:10,
and wherein the preparation is present as a hydrodispersion.

30. The preparation of claim 29, wherein the preparation comprises from 0.01% to about 1% by weight of creatine.

31. The preparation of claim 30, wherein the preparation comprises from 0.01% to about 1% by weight of creatinine.

32. The preparation of claim 29, wherein the one or more hydrocolloids comprise ammonium dimethyltauramide/vinylformamide copolymer.

33. The preparation of claim 31, wherein the one or more hydrocolloids comprise ammonium dimethyltauramide/vinylformamide copolymer.

34. The preparation of claim 31, wherein the preparation further comprises from 1% to 7% by weight of glycerin.

35. The preparation of claim 29, wherein the preparation comprises at least 0.1% by weight of the one or more hydrocolloids.

36. The preparation of claim 35, wherein the preparation comprises an aqueous phase which has a pH value of from about 6.5 to about 7.5.

37. The preparation of claim 29, wherein a weight ratio of creatinine to creatine is from 4:1 to 3:7.

\* \* \* \* \*